United States Patent [19]

Laszlo

[11] Patent Number: 5,331,547
[45] Date of Patent: Jul. 19, 1994

[54] PROCESS AND COMPUTER SYSTEM FOR CONTROL OF INTERFACE SOFTWARE AND DATA FILES

[75] Inventor: George Laszlo, White Plains, N.Y.

[73] Assignee: Clinical Multiphase Research, Inc., Wilton, Conn.

[21] Appl. No.: 11,309

[22] Filed: Jan. 29, 1993

[51] Int. Cl.⁵ .................................... G06F 15/403
[52] U.S. Cl. .................................. 364/413.01
[58] Field of Search ............. 364/413.01, 419.19, 364/146, 188; 235/462, 472, 495; 395/155, 156, 159, 161

[56] References Cited

U.S. PATENT DOCUMENTS

| | | | |
|---|---|---|---|
| 4,481,412 | 11/1984 | Fields | 235/472 |
| 4,550,247 | 10/1985 | Winter et al. | 235/472 |
| 4,652,733 | 3/1987 | Eng et al. | 235/462 |
| 4,703,412 | 10/1987 | Cuunningham et al. | 364/140 |
| 4,825,058 | 4/1989 | Poland | 235/472 |
| 4,831,610 | 5/1989 | Hoda et al. | 369/48 |
| 4,933,514 | 6/1990 | Bowers | 178/18 |
| 5,034,598 | 7/1991 | Poland | 235/435 |

Primary Examiner—Donald E. McElheny, Jr.

[57] ABSTRACT

A computer system and process with special application as a computer assisted new drug application in which a bar code reader is used to read command bar codes to manipulate user interface software and document retrieval bar codes to retrieve electronic documents.

23 Claims, 6 Drawing Sheets

PROCESS AND COMPUTER SYSTEM FOR CONTROL OF INTERFACE SOFTWARE AND DATA FILES

BACKGROUND OF THE INVENTION

(1) Field of the Invention

The present invention relates to a system permitting access to and control of a graphic user interface and data stored in a database or multiple databases.

(2) Description of the Prior Art

Computer users have increasingly embraced the use of various graphic user interfaces as the preferred method for computer control. A graphic user interface (hereafter referred to as a "GUI") permits the user to operate the many functions of the computer through a series of menus and manipulation of icons representing the desired function. The menus and icons are typically manipulated by movement of a cursor and activation, deactivation and movement of the menu selection or icon, which in turn causes operation of a desired software function. The graphic user interface is considered a substantial advance over prior computer command systems where extensive command terms had to be learned in order to effectively use the computer system. Despite these advances in improving the ease of use of a computer, there remains a substantial class of persons who are unwilling to devote the time needed to learn the effective use of computer systems. The present invention provides a method and apparatus for controlling computer functions that requires fewer learned computer skills than even a conventional GUI.

SUMMARY OF THE INVENTION

A process and computer system for controlling graphic user interface software and accessing data files in a computer system, which includes an optical image reading device and software. The invention permits operation of the interface software by simply reading predetermined code symbols with the reader to thereby activate various computer functions and/or to retrieve electronic documents and display them for the operator.

The system reads a printed code symbol in at least base 16 to create a read-in alphanumeric code in at least base 16; this alphanumeric code is stored in a temporary buffer memory which is polled and then tested to assure that the stored code is complete. The alphanumeric code is translated into a base 10 code which has a preassigned object identification. The object identification is compared with an object table to determine if the object identification is a control code for the graphic user interface software or a document request code. If the object identification is a control code, then the base 10 control code is matched to a corresponding internal event identification code, and a message containing the internal event identification code is sent for detection in a main event loop of the graphic user interface software where the graphic user interface software interprets and executes the message to control a user interface function. If the object identification is a document request code, then a search query is composed and sent to a search engine residing in the computer system to execute and retrieve the requested document and display the requested document on an output device.

In the preferred embodiment, the printed code is a bar code and the image scanner is a bar code reader such as a wand.

The code is rendered in at least base 16 and preferably base 32 or higher, most preferably base 64, to permit short bar code "words" that relate to a far larger universe of possible object identifications than would be possible in base 10.

In one preferred embodiment, the process and system comprise a registration document submitted to a government agency such as a regulatory agency. In a most preferred embodiment, they comprise a new drug application submitted to obtain approval of a new drug by the Food & Drug Administration, and includes a hard copy application or report that include printed code symbols that can be read with a bar code reader to obtain and display data such as supporting data, graphs, studies, monographs, analyses or the like relating to the text of the new drug application.

Further objects and details of the present invention can be seen from the accompanying drawings and detailed description of the preferred embodiment set forth below.

BRIEF DESCRIPTION OF THE DRAWINGS

FIGS. 1—1 to 1-4 are schematic flowcharts showing the operation of the process and computer system of the invention.

FIG. 2 is a reproduction of a control card for use in controlling user interface software.

FIG. 3 is a reproduction of a document demonstrating the application of the invention to a new drug application.

DETAILED DESCRIPTION OF THE PREFERRED EMBODIMENT

Figure 1A:
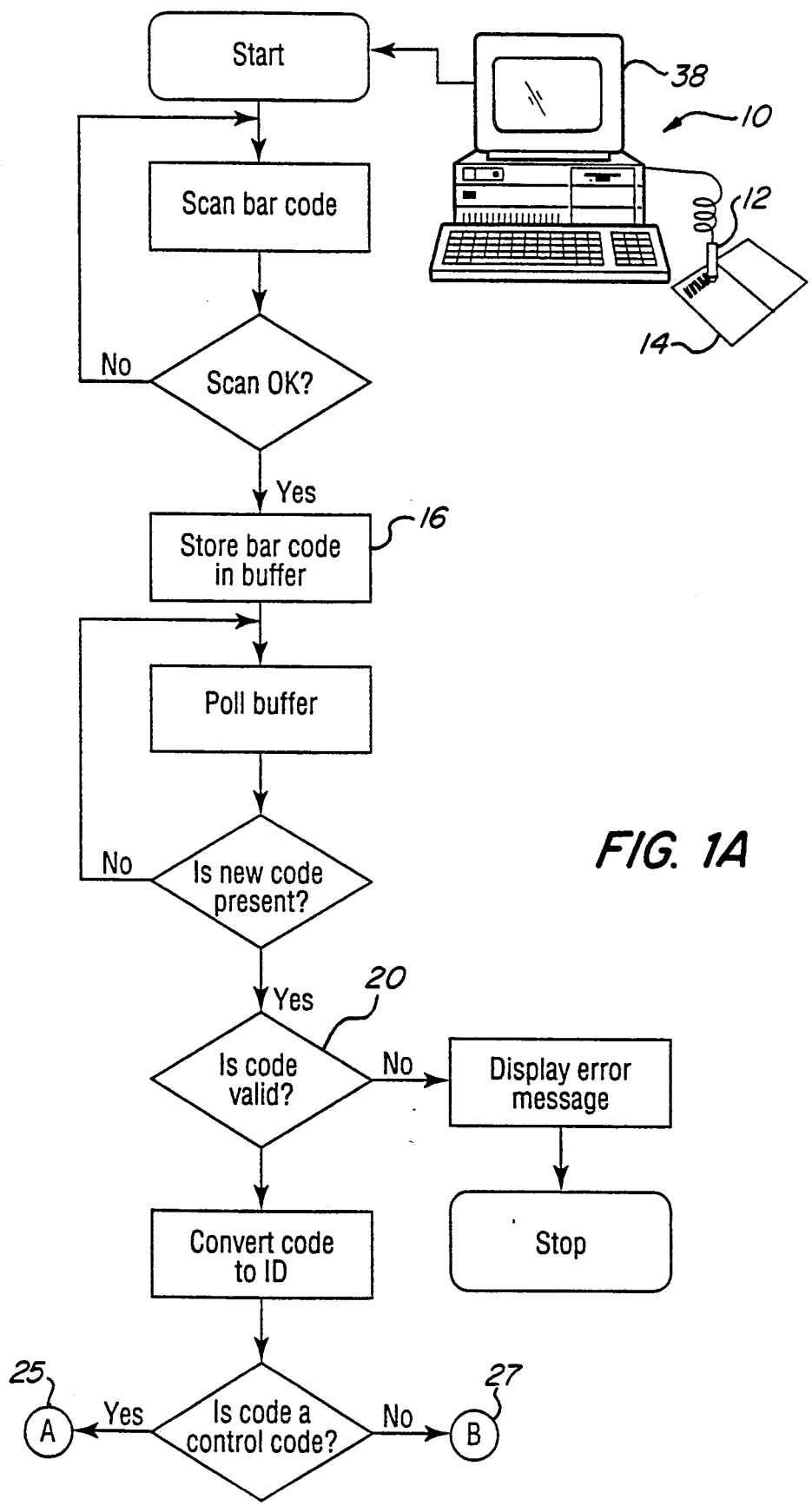
Figure 1B:
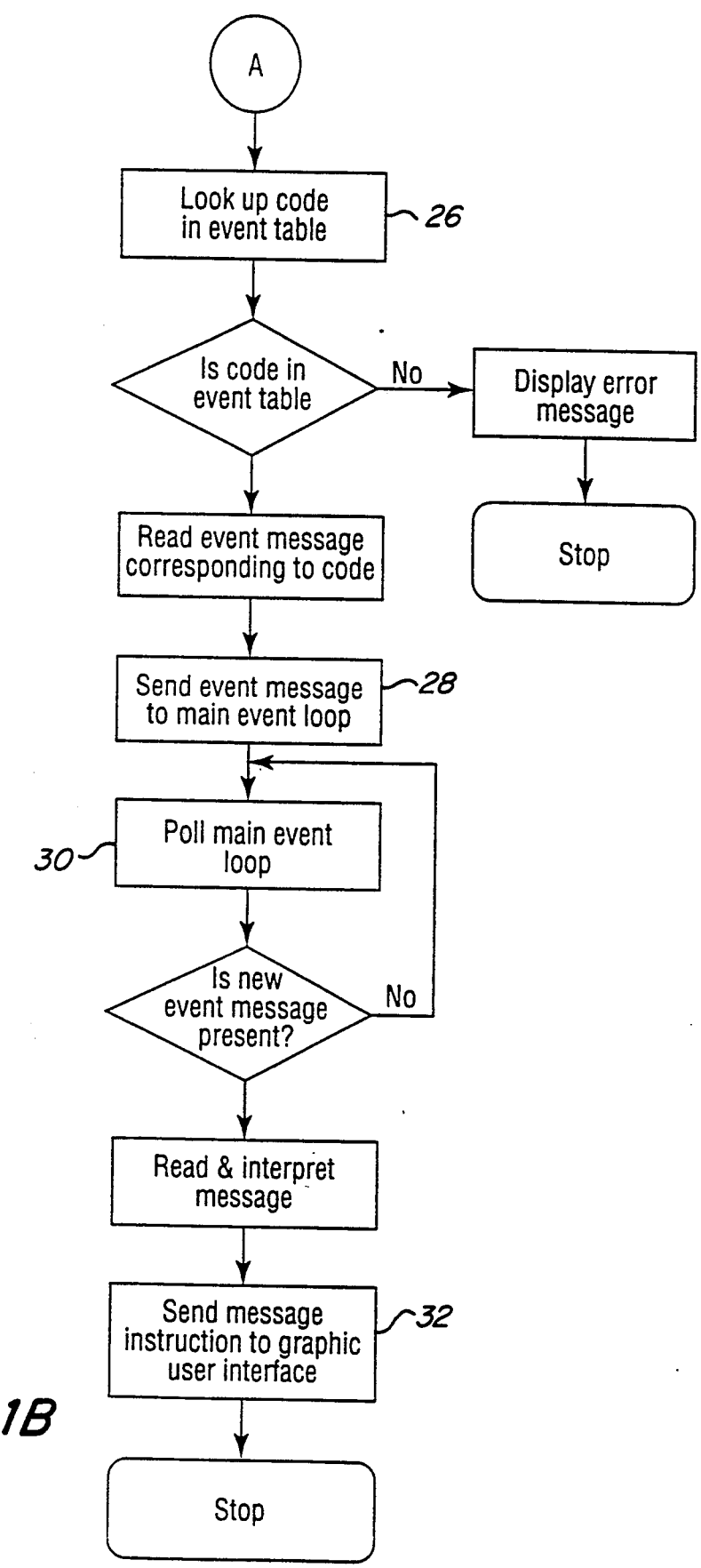
Figure 1C:
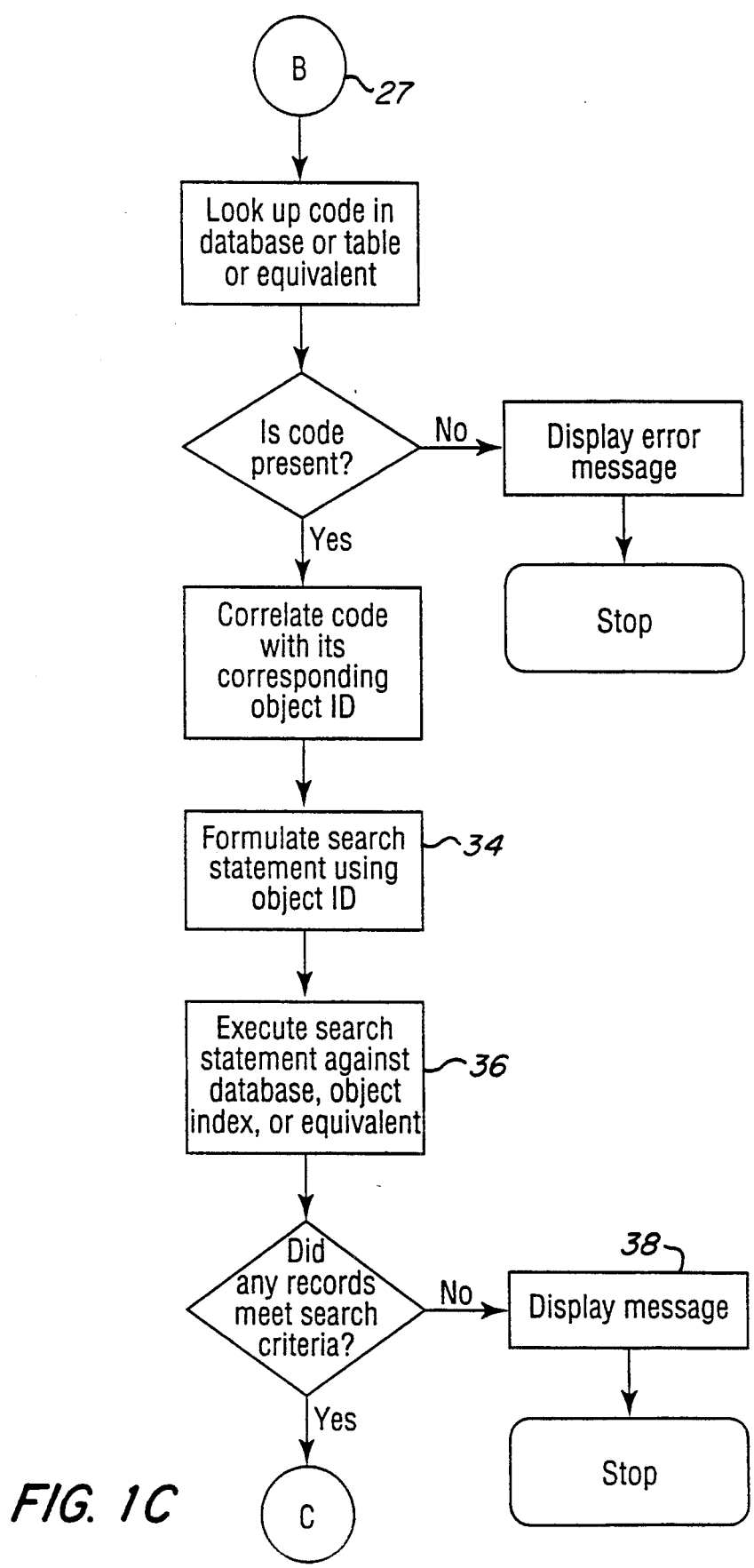
Figure 1D:
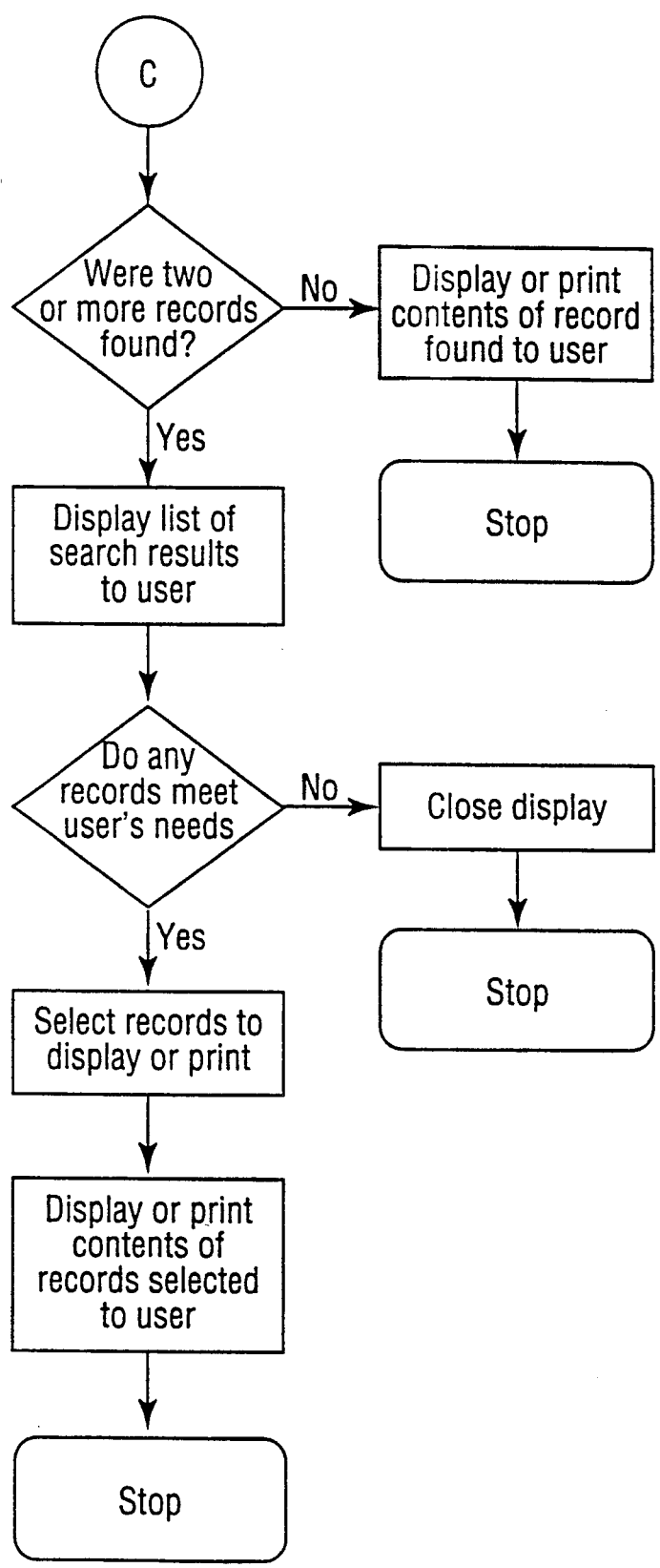

As used herein, a "computer system" comprises at least the following components: a central processing unit (CPU), a display device, a storage device, and a printing capability. Preferably, the CPU is working in a client/server operating environment. The storage device can include both electronic memory and CD-ROM optical disk storage. Preferably the CPU is provided with modem access to external databases.

As used herein "hard copy document" means a printed document, a paper document, or other tangible fixed work.

As used herein "document" means any kind of information-containing object such as a data file stored in a database and/or optical disk storage, including but not limited to written documents, articles, reports and correspondence; graphic and video still and moving images, illustrations, charts, tables, and graphs; audio records including narrative, speeches, music and other audio information.

As used herein, "user interface" means the hardware and software that permits the computer operator to manipulate a computer operating system and specific documents stored on the computer.

As used herein, "graphic user interface software" means software for manipulation of a computer operating system by using a cursor to select and activate various operating system functions.

The present invention permits operation of the computer system by simply reading predetermined code symbols with an image reader to thereby activate various computer functions and/or to retrieve electronic documents and display them for the operator.

Referring now to FIG. 1, a computer system 10 for control of a graphic user interface and for accessing data files in accordance with the invention is provided with an optical image reader 12 for scanning a code symbol 14.

The code symbol 14 will typically be a bar code, and the image reader 12 is a bar code reader such as a light pen or wand and/or a laser scanner.

The code symbol 14 comprises a code in at least base 16 and preferably base 32 or higher, and most preferably in base 64. The use of non-base 10 code permits short bar code "words" that identify a far larger universe of possible object identifications than would be possible in base 10. For example, a five digit word in base 10 identifies up to 99,999 different objects, while a five digit word in base 16 identifies 1,048,575 different objects, a five digit word in base 32 identifies 33,554,431 different objects, and a five digit word in base 64 identifies up to 1,073,741,824 different objects. Since it is desirable to compress as much information as possible into a small printed area in a hard copy document, a high number base is preferred.

Code symbol 14 is read-in as an alphanumeric code in the original base of the code symbol 14, and is stored in a temporary buffer memory 16.

A computer subprogram resident in the computer system periodically polls the buffer memory 16 to determine if an alphanumeric code is stored in the buffer memory 16. If the buffer 16 indicates a stored code, the stored alphanumeric code is tested using a validation protocol subprogram 20 to assure that the stored code is a complete code. A tested and validated stored code is then translated by a subprogram to a base 10 object identification code 22.

The object identification code is then compared by a subprogram with a list of preassigned object identifications in an object table 24 to determine if the object identification 22 is a control code 25 for graphic user interface software resident on the computer system or a document request code 27. This determination is made by examining a preselected field in the object identification code to determine if the numbers in the field correspond to certain numbers which are reserved for control codes 25.

If the object identification is determined to be a control code 25, then a subprogram 26 matches the base 10 control code to a corresponding internal event identification code. The internal event identification code links the control code to the native instruction set inherent to a graphic user interface software. The subprogram 26 composes a message 28 using the internal event identification code for detection in a main event loop 30 of the graphic user interface software 32. Message 28 may be either sent to a message area in the main event loop 30 which is periodically polled by the software, or the message 28 may interrupt the main event loop 30. The graphic user interface software then receives, interprets and executes the message 28 to execute a user interface function.

Figure 2:
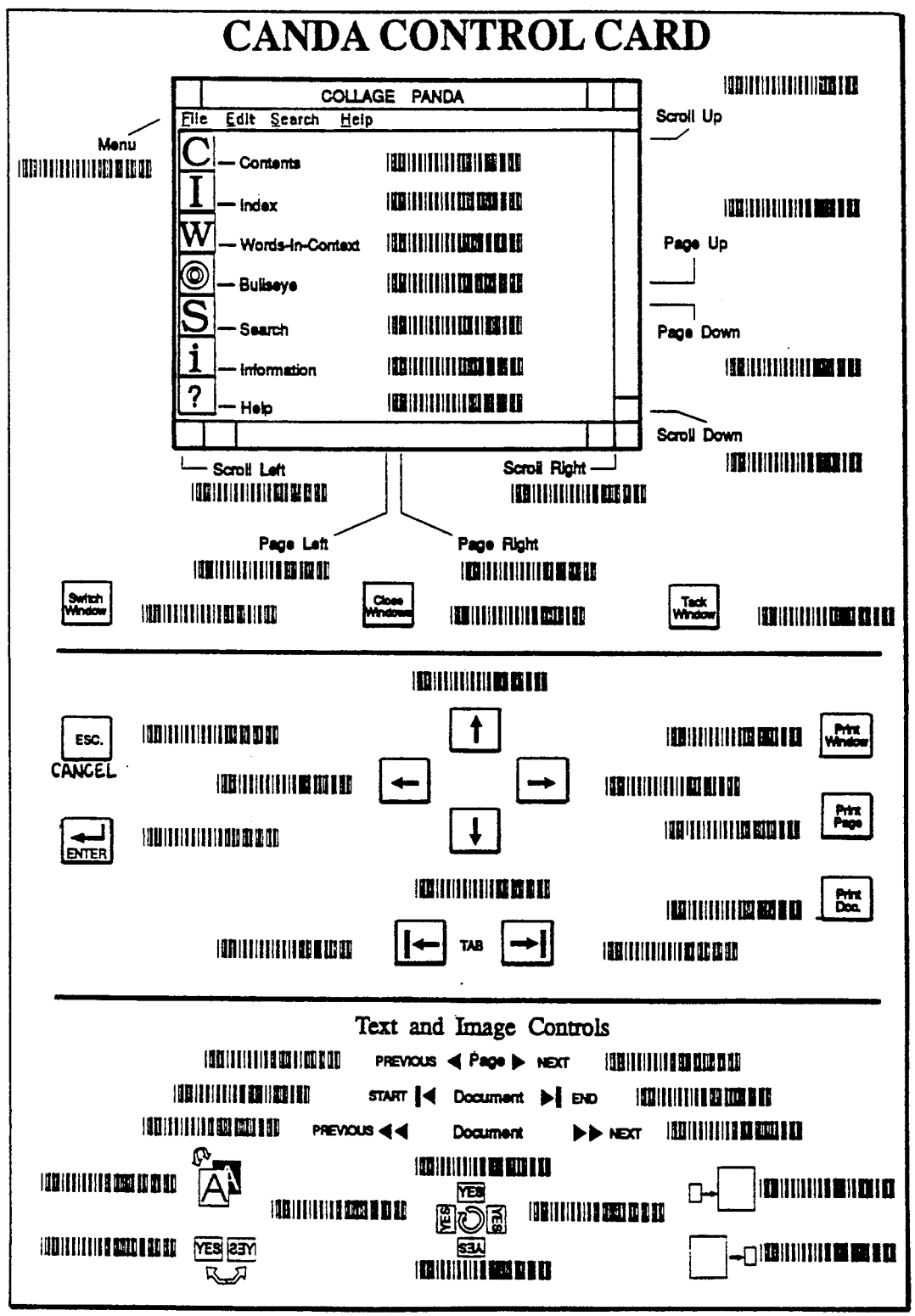
Figure 3:
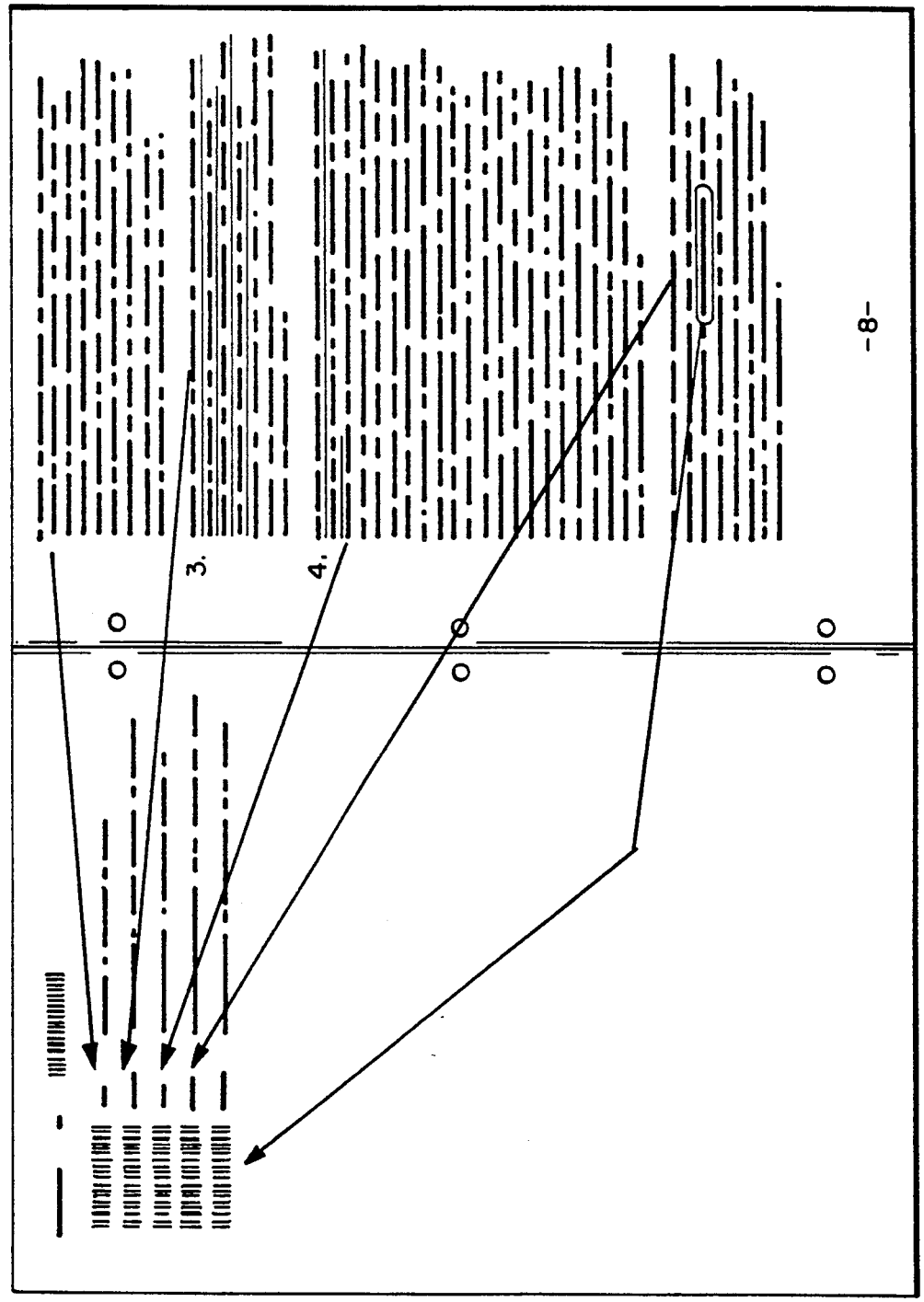

Referring to FIG. 2, a typical control card is shown. The user of the computer system would simply read in the desired function using a bar code reader and the computer system would operate as described to execute the desired function.

The user interface functions to be controlled by the internal event identification code and executed by the interface software can typically include one or more of the following: open window, close window, pull down menu, escape window, start help, increase window size, decrease window size, scroll up, scroll down, page up, page down, scroll left, scroll right, page left, page right, print window content, print page, print document, tab left, tab right, next page, previous page, next document, previous document and rotate image.

If the object identification 22 is a document request code 27, then a subprogram 34 composes a search query using the object identification for execution by a search engine 36 resident on the computer system. The search engine 36 locates the requested document and causes it to be displayed on an output device such as a terminal display 38. The document request code would find a corresponding database record or object which would typically include fields identifying the location of the stored document (i.e. the storage device), the type of document (i.e. ASCII file, raster image file, Wordperfect file etc. ), and the identity of the specific document.

The search engine is a document retrieval application software having access to computer files residing in electronic memory storage and optical memory storage devices operatively connected with the computer system 10. The requested document may take any of the forms as defined above. The document may be stored on computer data files, image files, databases, imagebases, and CD-ROM optical disk files. Potential output devices include a display screen, sound generation equipment, a printer or a plotter.

The computer system is provided with database management or object tracking software to automatically generate and keep track of the object identifications, and where the objects are located, so that the same object identifications are not assigned to different objects. This software also permits the linkage of hard copy documents to their electronic equivalents or related objects and allows the printing of a hard copy document with relevant code symbols in place. This links the hard copy document to documents that can be requested from the computer system and displayed on computer monitors or other output devices.

A process in accordance with the invention comprises the steps set forth above, which requires reading a printed code symbol to create a read-in alphanumeric code; this alphanumeric code is stored in a temporary buffer memory which is polled and then tested to assure that the stored code is complete. The alphanumeric code is translated into a base 10 code which has a preassigned object identification. The object identification is compared with an object table to determine if the object identification is a control code for the graphic user interface software or a document request code. If the object identification is a control code, then the base 10 control code is matched to a corresponding internal event identification code, and a message containing the internal event identification code is sent for detection in a main event loop of the graphic user interface software whereby the graphic user interface software interprets and executes the message to control a user interface function. If the object identification is a document request code, then a search query is composed and sent to a search engine residing in the computer system to execute and retrieve the requested document and display the requested document on an output device.

In one preferred embodiment, the computer system and process are applied to create a registration or application document submitted to a government agency. For example, this might comprise a new drug application submitted to obtain approval of a new drug by the Food & Drug Administration. This could include a hard copy document such as an application or report that includes printed code symbols that can be read with a bar code reader to obtain and display documents such as supporting data, graphs, studies, monographs, analyses or the like relating to the text of the new drug application. These documents are assigned object identifications by the user either in advance of preparation of a text or during or subsequent to preparation of a text. The user is presented with each object and the user defines what type of object it is while the object tracking software defines the location of the object.

In such case, the object tracking software can be set up to print a relevant code symbol embedded in the text of the application, or to print the code symbol on the facing page of each page of a bound application. The object tracking software permits linkages to be established between different documents and assists in locating requested objects.

It is to be appreciated that the foregoing is illustrative and not limiting of the invention, and that various changes and modifications to the preferred embodiments described above will be apparent to those skilled in the art. Such changes and modifications can be made without departing from the spirit and scope of the present invention, and it is therefore intended that such changes and modifications be covered by the following claims.

I claim:

1. A process for controlling graphic user interface software and accessing data files in a computer system, comprising the steps of:

reading a code symbol using an optical image reading device to create a read-in code, said read-in code comprising an alphanumeric code in at least base 32;

storing the alphanumeric code in a temporary buffer memory;

polling the buffer at periodic intervals to determine whether an alphanumeric code is stored therein;

testing the alphanumeric code using a validation protocol to assure that the stored code is complete;

translating the alphanumeric code into a base 10 code, said base 10 code comprising an object identification;

comparing the object identification with an object table to determine if the object identification is a control code for the graphic user interface software or a document request code; and if the object identification is a control code, then implementing the following steps:

matching the base 10 control code to a corresponding internal event identification code, and composing a message from said internal event identification code for detection in a main event loop of the graphic user interface software whereby said graphic user interface software interprets and executes the message to control user interface functions; and if the object identification is a document request code, then implementing the following steps:

composing a search query using said object identification for execution by a search engine residing in said computer system, and executing said search query to locate and display the requested document on an output device.

2. A process in accordance with claim 1, wherein said message composed from said internal event identification code for execution to control user interface functions is effective to operate a function selected from the set comprising open window, close window, pull down menu, escape window, start help, increase window size, decrease window size, scroll up, scroll down, page up, page down, scroll left, scroll right, page left, page right, print window content, print page, print document, tab left, tab right, next page, previous page, next document, previous document and rotate image.

3. A process in accordance with claim 1, wherein said requested document comprises an electronic object selected from the set comprising computer data files, image files, databases, imagebases, and CD-ROM disk files.

4. A process in accordance with claim 3, wherein said output device is selected from the set comprising a display screen, sound generation equipment, and a printer.

5. A process in accordance with claim 4, wherein said code symbol is a bar code symbol, readable by a bar code reader.

6. A process in accordance with claim 4, wherein said read-in code comprises an alphanumeric code in base 39.

7. A process in accordance with claim 4, wherein said read-in code comprises an alphanumeric code in base 64.

8. A process in accordance with claim 5, wherein said bar code symbol is affixed to a hard copy document wherein a user of the computer system may operate the system and access data files relating to said hard copy document using the said bar code symbols.

9. A process in accordance with claim 8, wherein said hard copy document comprises a document submitted to a government agency and relates to a product for human consumption.

10. A process in accordance with claim 9, wherein said hard copy document comprises an application document made to obtain approval of a medical product prior to public distribution, and said related data files comprise test data and related analysis.

11. A computer system for control of a graphical user interface and for accessing data files, comprising:

an optical image reading device for scanning a code, said read-in code symbol comprising an alphanumeric code in at least base 32;

a temporary buffer memory for storing the alphanumeric code;

a computer subprogram for periodic polling of the buffer memory to determine if an alphanumeric code is stored in the buffer memory;

a computer program for testing the alphanumeric code using a validation protocol to assure that the stored code is complete;

a computer program for translating the alphanumeric code into a base 10 code, said base 10 code comprising an object identification;

a computer program for comparing the object identification with an object table to determine if the object identification is a control code for the graphic user interface software or a document request code; and if the object identification is a control code, then implementing the following steps:

matching the base 10 control code to a corresponding internal event identification code, and composing a message from said internal event identification code for detection in a main event loop of the graphic user interface software whereby said graphic user interface software interprets and executes the message to control user interface functions; and if the object identification is a document request code, then implementing the following steps:

composing a search query using said object identification for execution by a search engine residing in said computer system, and executing said search query to locate and display the requested document on an output device.

12. A computer system in accordance with claim 11, wherein said search engine comprises document retrieval application software having access to computer files residing in electronic memory storage and optical memory storage devices operatively connected with said computer system.

13. A computer system in accordance with claim 12, further comprising database management or object tracking software to generate and record the object identifications and the documents corresponding to the object identifications.

14. A computer system in accordance with claim 13, wherein said code symbol is a bar code symbol, readable by a bar code reader.

15. A computer system in accordance with claim 14, wherein said bar code symbol is affixed to a hard copy document wherein a user of the computer system may operate the system and access data files relating to said hard copy document using the said bar code symbols.

16. A process in accordance with claim 15, wherein said hard copy document comprises a document submitted to a government agency and relates to a product for human consumption.

17. A computer system in accordance with claim 16, wherein said hard copy document comprises an application document made to obtain approval of a medical product prior to public distribution, and said related data files comprise test data and related analysis.

18. A computer-assisted new drug application comprising:

a hard copy document including a plurality of code symbols affixed thereto, said code symbol comprising a code in at least base 32;

a computer system including data storage devices with electronic documents relating to said hard copy document stored therein, and having graphic user interface software;

an optical image reading device operatively connected to said computer system for reading said code symbols and storing an alphanumeric code in at least base 32 corresponding to said code symbols in a temporary buffer memory;

said computer system having a polling program and circuit for polling the buffer memory at periodic intervals to determine whether an alphanumeric code is stored therein;

said computer system having a computer program for testing the alphanumeric code using a validation protocol to assure that the stored code is complete;

said computer system having a translating program for translating the alphanumeric code into a base 10 code comprising an object identification;

said computer system having an object tracking program for generating object identifications and keeping track of the location of documents stored in said data storage devices;

said computer system having a computer program for comparing the object identification with an object table to determine if the object identification is a control code for the graphic user interface software or a document request code; and, if the object identification is a control code, then implementing the following steps:

matching the base 10 control code by a look-up table to a corresponding internal event identification code, and composing a message from said internal event identification code for detection in a main event loop of the graphic user interface software whereby said graphic user interface software interprets and executes the message to control user interface functions; and if the object identification is a document request code, then implementing the following steps:

composing a search query using said object identification for execution by a search engine residing in said computer system, and executing said search query to locate and display the requested electronic document on an output device.

19. An application in accordance with claim 18, wherein said message composed from said internal event identification code for execution to control user interface functions is effective to operate a function selected from the set comprising open window, close window, pull down menu, escape window, start help, increase window size, decrease window size, scroll up, scroll down, page up, page down, scroll left, scroll right, page left, page right, print window content, print page, print document, tab left, tab right, next page, previous page, next document, previous document and rotate image.

20. An application in accordance with claim 18, wherein said requested electronic document comprises an electronic object selected from the set comprising computer data files, image files, databases, imagebases, and CD-ROM disk files.

21. An application in accordance with claim 20, wherein said output device is selected from the set comprising a display screen, sound generation equipment, and a printer.

22. An application in accordance with claim 21, wherein said code symbol is a bar code symbol, readable by a bar code reader.

23. A process in accordance with claim 22, wherein said code symbol comprises a code in base 64.

* * * * *